(12) United States Patent
Chang et al.

(10) Patent No.: US 9,867,984 B2
(45) Date of Patent: Jan. 16, 2018

(54) FLUORIDE IONTOPHORESIS DEVICE AND METHOD THEREOF

(71) Applicant: NATIONAL TAIWAN UNIVERSITY, Taipei (TW)

(72) Inventors: Che-Chen Chang, Taipei (TW); Bor-Shiunn Lee, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 9 days.

(21) Appl. No.: 14/735,832

(22) Filed: Jun. 10, 2015

(65) Prior Publication Data

US 2016/0106972 A1    Apr. 21, 2016

(30) Foreign Application Priority Data

Oct. 20, 2014    (TW) .............................. 103136177 A (51) Int. Cl.
*A61N 1/04* (2006.01)
*A61N 1/32* (2006.01)
*A61N 1/05* (2006.01)

(52) U.S. Cl.
CPC ............ *A61N 1/325* (2013.01); *A61N 1/0428* (2013.01); *A61N 1/0548* (2013.01)

(58) Field of Classification Search
CPC ..... A61N 1/325; A61N 1/0428; A61C 19/063
See application file for complete search history.

(56) References Cited

U.S. PATENT DOCUMENTS

| 4,149,533 A * | 4/1979 | Ishikawa ................ A61C 19/06 604/20 |
| 2004/0267190 A1 | 12/2004 | Tamarkin et al. |
| 2013/0072851 A1 * | 3/2013 | Doll .......................... A61N 1/32 604/20 |

FOREIGN PATENT DOCUMENTS

TW    401309    8/2000

OTHER PUBLICATIONS

Taiwanese Office Action, dated Jun. 20, 2016, in a counterpart Taiwanese patent application, No. TW 103136177.

* cited by examiner

*Primary Examiner* — Eric D. Bertram
(74) *Attorney, Agent, or Firm* — Chen Yoshimura LLP (57) ABSTRACT

The present invention provides a device for fluoride iontophoresis, comprising at least one electrochemical cell device containing at least one electrode and a fluoride-containing electrolyte, wherein the electrode is operated via an electromotive force to drive the fluoride-containing electrolyte into a biological interface; and a power supply connecting electrically to the cell device and at least providing a periodic pulse voltage signal to the electrode.

6 Claims, 15 Drawing Sheets

| | | | | |
|---|---|---|---|---|
| PA (OCV$_{0.002s}$-10V$_{0.008s}$) | A 0.12 | A 0.13 | A 0.09 | |
| | B 0.06 | B 0.07 | B 0.07 | |
| | C 0.07 | C 0.08 | C 0.08 | |
| | D 0 | D 0.04 | D 0.04 | |
| PA (OCV$_{0.005s}$-10V$_{0.005s}$) | A 0.24 | A 0.17 | A 0.23 | A 0.23 |
| | B 0.2 | B 0.16 | B 0.19 | B 0.20 |
| | C 0.16 | C 0.11 | C 0.15 | C 0.13 |
| | D 0.12 | D 0.09 | D 0.13 | D 0.12 |
| PA (OCV$_{0.005s}$-10V$_{0.02s}$) | A 0.25 | A 0.25 | A 0.27 | |
| | B 0.19 | B 0.21 | B 0.22 | |
| | C 0.18 | C 0.17 | C 0.15 | |
| | D 0.12 | D 0.11 | D 0.13 | |
| PA (OCV$_{0.005s}$-10V$_{0.08s}$) | A 0.24 | A 0.23 | A 0.23 | |
| | B 0.21 | B 0.18 | B 0.21 | |
| | C 0.18 | C 0.17 | C 0.18 | |
| | D 0.11 | D 0.15 | D 0.16 | |
| PA (OCV$_{0.005s}$-10V$_{0.32s}$) | A 0.26 | A 0.25 | A 0.25 | |
| | B 0.22 | B 0.21 | B 0.22 | |
| | C 0.17 | C 0.18 | C 0.17 | |
| | D 0.15 | D 0.16 | D 0.16 | |
| PA (OCV$_{0.008s}$-10V$_{0.002s}$) | A 0.04 | A 0.07 | A 0.05 | |
| | B 0.03 | B 0.04 | B 0.05 | |
| | C 0.03 | C 0.05 | C 0.05 | |
| | D 0.02 | D 0.02 | D 0.04 | |
| PA (OCV$_{0.02s}$-10V$_{0.005s}$) | A 0.22 | A 0.21 | A 0.21 | |
| | B 0.18 | B 0.19 | B 0.19 | |
| | C 0.15 | C 0.15 | C 0.14 | |
| | D 0.07 | D 0.06 | D 0.04 | |
| PA (OCV$_{0.08s}$-10V$_{0.005s}$) | A 0.23 | A 0.20 | A 0.22 | |
| | B 0.16 | B 0.18 | B 0.19 | |
| | C 0.14 | C 0.13 | C 0.15 | |
| | D 0.11 | D 0.09 | D 0.12 | |
| PA (0V$_{0.005s}$-10V$_{0.005s}$) | A 0.21 | A 0.12 | A 0.18 | |
| | B 0.16 | B 0.12 | B 0.17 | |
| | C 0.14 | C 0.10 | C 0.13 | |
| | D 0.13 | D 0.07 | D 0.12 | |
| PA (5V$_{0.005s}$-10V$_{0.005s}$) | A 0.19 | A 0.19 | A 0.24 | A 0.16 |
| | B 0.18 | B 0.14 | B 0.14 | B 0.12 |
| | C 0.13 | C 0.14 | C 0.08 | C 0.07 |
| | D 0.11 | D 0.12 | D 0.10 | D 0.09 |
| PA (-5V$_{0.005s}$-10V$_{0.005s}$) | A 0.15 | A 0.19 | A 0.12 | A 0.13 |
| | B 0.13 | B 0.17 | B 0.09 | B 0.1 |
| | C 0.11 | C 0.13 | C 0.10 | C 0.06 |
| | D 0.10 | D 0.14 | D 0.07 | D 0.05 |
| CA | A 0.19 | A 0.14 | A 0.13 | |
| | B 0.11 | B 0.12 | B 0.12 | |
| | C 0.09 | C 0.08 | C 0.07 | |
| | D 0.03 | D 0.07 | D 0.05 | |

FLUORIDE IONTOPHORESIS DEVICE AND METHOD THEREOF

INCORPORATION BY REFERENCE

This application claims priority from R.O.C. Patent Application No. 103136177, filed on Oct. 20, 2014, the contents of which are hereby incorporated by reference in their entirety for all purposes.

TECHNICAL FIELD

The present invention relates to a pulse iontophoresis device, and particularly relates to a fluoride iontophoresis device applied to teeth.

BACKGROUND

At present, a conventional fluoride application (CFA) is used to prevent teeth from demineralization. The process of CFA is to apply colloidal fluoride over a patient's teeth directly and form $CaF_2$ compounds on the teeth. However, many literatures have found that $CaF_2$ compounds can't stay on the teeth for twenty-four hours, so the effect of CFA is limited.

At present, iontophoresis is used as a dental treatment. The principle of iontophoresis is to import electrified medicines into a patient's body by applying an external electric field. Iontophoresis is often used to import electrified medicines into a patient's skin, and the positive effect of iontophoresis has been confirmed.

Iontophoresis has been applied to teeth and imported fluorides into the teeth to prevent the teeth from demineralization. In addition, a previous research reported NaF iontophoresis. NaF iontophoresis imports fluorides into dentinal tubules to produce precipitation of $CaF_2$ by electric voltage. The fluid movement in dentinal tubules is reduced by precipitation of $CaF_2$, thereby the purpose of reducing dentin hypersensitivity can be achieved. However, application of iontophoresis to the teeth still has many problems. For example, the architecture of teeth is very different from that of skin, wherein the skin has more pores and the drug transportation into skin is better.

Figure 1A:
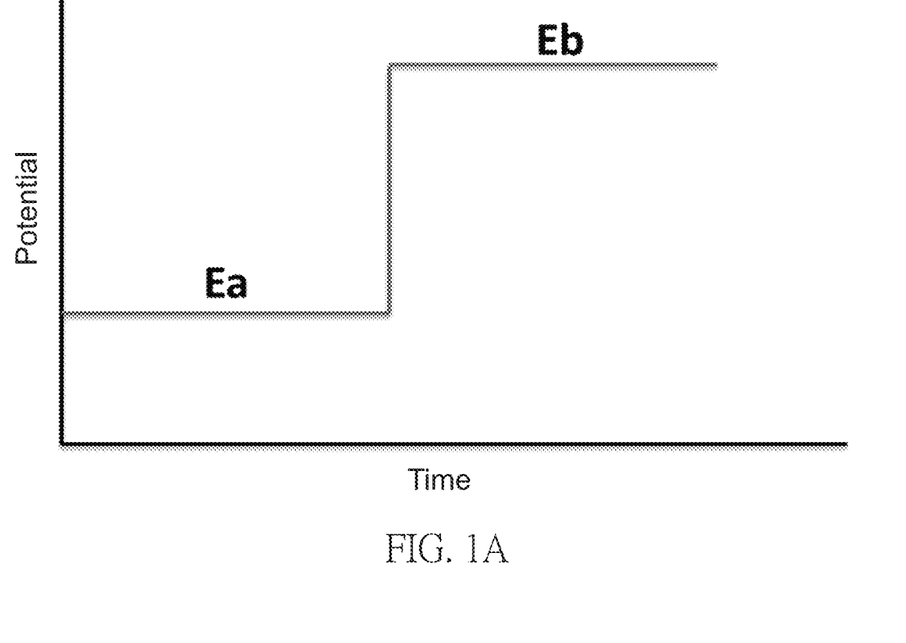
FIG. 1A and FIG. 1B respectively show time functions of the potential and the current in chronoamperometry.
Figure 1B:
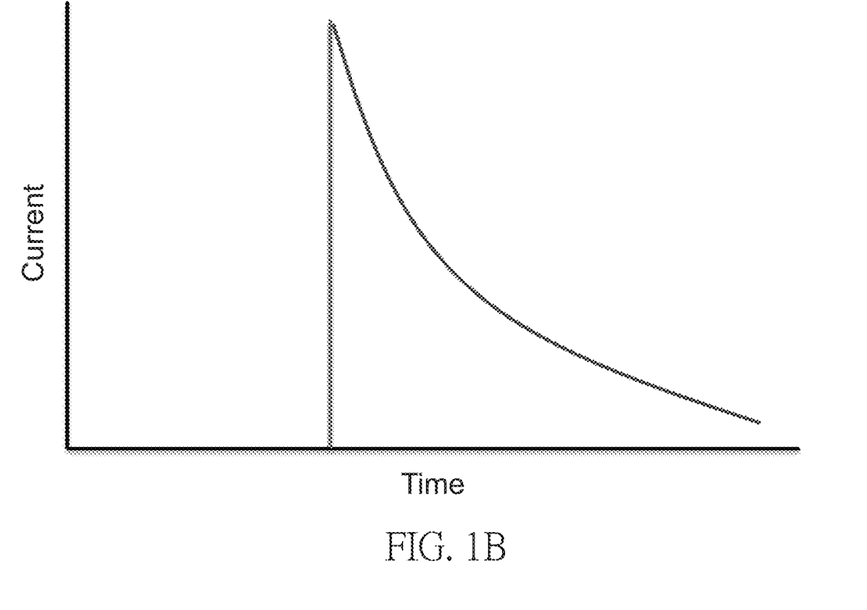

An electrochemical approach of a current commercial fluoride iontophoresis (FI) device (Pyo-cure, Narcohm, Japan) is based on chronoamperometry (CA). The principle of CA is to provide fixed potentials at different instants, as shown in FIG. 1A, which shows a time-dependent function of potential. The corresponding time function of current is shown in FIG. 1B. As shown in FIG. 1A, when oxidation-reduction substances exist in the system and the potential is fixed at Ea, no oxidation-reduction reaction take place. When the potential is elevated and fixed to Eb, a reduction reaction occurs rapidly, resulting in a rapid decrease of the concentration of the redox substances diffusing to the surface of the working electrode to zero.

The drawbacks of the current commercial FI device include a limited degree of incorporation of fluoride and the failure to import fluoride into inner part of the teeth. They affect the efficiency of the intended demineralization prevention. For example, the duration that fluorine compounds staying in the teeth can't thus be prolonged.

Therefore, there is a need for an improved fluoride iontophoresis to address at least the foregoing issues.

SUMMARY

The present invention provides a pulse fluoride iontophoresis device comprising at least one electrochemical cell device containing at least one electrode and a fluoride-containing electrolyte, the electrode is operated via an electromotive force to import the fluoride-containing electrolyte into a biological interface; and a power supply connecting electrically to the cell device and at least providing a periodic pulse voltage to the electrode.

This pulse fluoride iontophoresis device can import fluorides into the inner part of the teeth, form stable fluorapatite (FAP) in the teeth through the ion exchange reaction occurring in hydroxyapatites (HAP) of the teeth, and prolong the duration of fluorine compounds present in the teeth.

BRIEF DESCRIPTION OF THE DRAWINGS

Exemplary embodiments will be more readily understood from the following detailed description when read in conjunction with the appended drawing, in which.

DETAILED DESCRIPTION

Figure 4A:
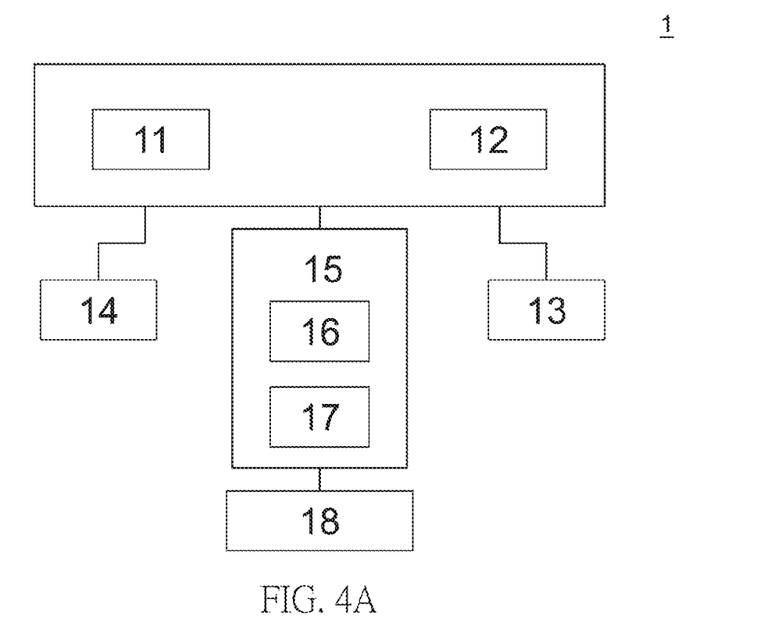
FIG. 4A and FIG. 4B show one embodiment of an electrochemical cell device according to the present invention.

FIG. 4A shows one embodiment of a fluoride iontophoresis device 1 according to the present invention. The fluoride iontophoresis device 1 comprises a power supply 11, a current conducting device 12, a reference electrode 13, an auxiliary electrode 14, and a working electrode 15, wherein the working electrode 15 includes an electrode 16 and a fluoride-containing electrolyte 17, and the working electrode 15 is contact with a biological interface 18.

In this embodiment, the biological interface 18 is a tooth, and the fluoride-containing electrolyte 17 is sodium fluoride (NaF), to which the fluoride-containing electrolyte 17 is not limited, though. The fluoride-containing electrolyte may be in the liquid or gelation state. In one embodiment, the fluoride-containing electrolyte 17 may be in the liquid state, and the electrode 16 is in contact with the biological interface 18 in the fluoride-containing electrolyte 17. In another embodiment, the fluoride-containing electrolyte 17 may be in the state of gelation, which can be applied over the surface of the electrode 16 and in contact with the biological interface 18.

The power supply 11 may output a periodic pulse voltage. The pulse voltage has a plurality of pulse periods, and each of the pulse periods is composed of a base potential and a pulse potential. During each of the pulse periods, the base potential can be elevated to the pulse potential instantly or slowly. In this embodiment, the fluoride iontophoresis device adopts pulse amperometry (PA) to import fluorides into a target. For example, the target can be a tooth.

Figure 3:
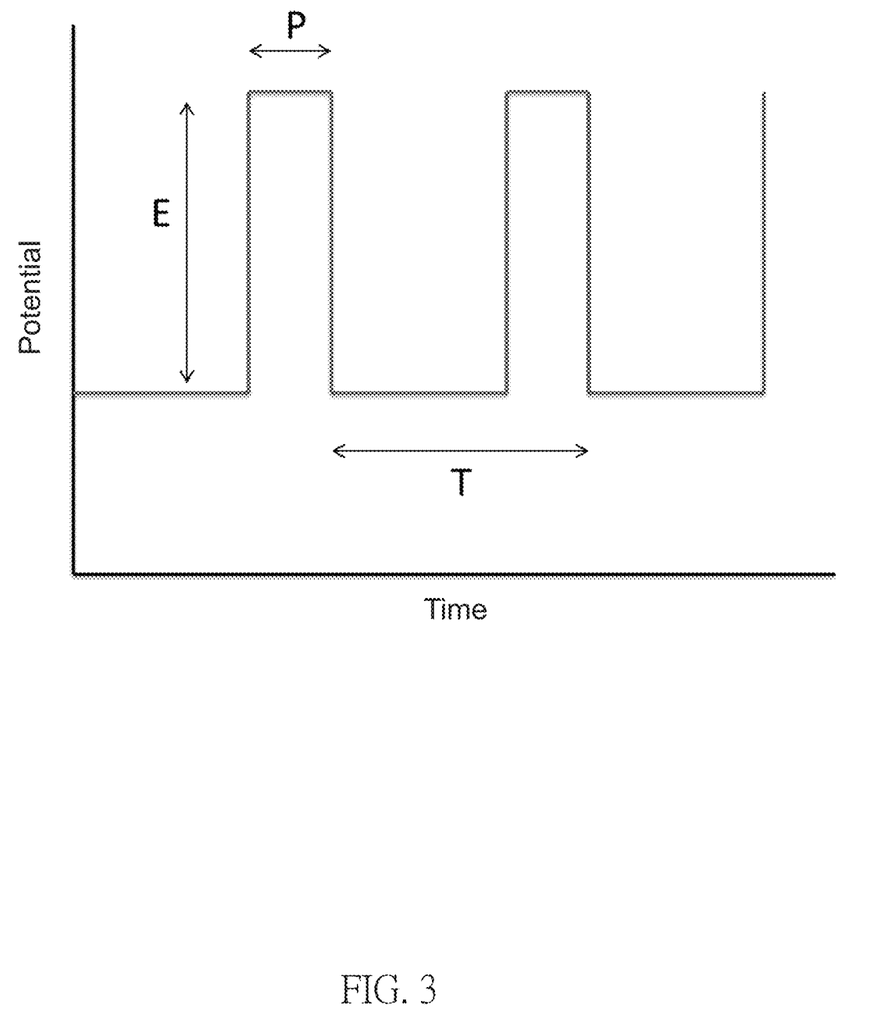
FIG. 3 shows the time function of the potential in pulse amperometry (PA)

FIG. 3 shows a time function of potential of the adopted pulse amperometry (PA). The base potentials and pulse potentials during any two of neighboring pulse periods may be the same or different. The mode of potential application in the pulse amperometry starts from a base potential, and the potential may then be elevated as a square wave superimposed on a staircase wave to a pulse potential, the sum of the durations of the base potential and the pulse potential is a pulse period (T), and the duration of the pulse potential is a pulse width (P). In one embodiment, the base potential and the pulse potential remain the same during the plurality of pulse periods. In another embodiment, the base potentials and the pulse potentials are varied gradually during the plurality of pulse periods.

A ratio of the durations of the base potential and the pulse potential is between 1:64 and 64:1 during one pulse period. For example, the ratio of the durations of the base potential and the pulse potential can be 1:1, 1:4, 1:5, 1:16, 1:64, 4:1, 5:1, 16:1, or 64:1.

The duration of the base potential is between 0.001 second and 0.32 second during one pulse period. For example, the duration of the base potential can be 0.001 second, 0.002 second, 0.005 second, 0.008 second, 0.02 second, 0.08 second, or 0.32 second, or the duration between any two durations shown above. In another better embodiment, the duration of the base potential is between 0.002 second and 0.08 second.

The duration of the pulse potential is between 0.001 second and 0.32 second. For example, the duration of the pulse potential can be 0.001 second, 0.002 second, 0.005 second, 0.008 second, 0.02 second, 0.08 second, or 0.32 second, or the duration between any two durations shown above. In another better embodiment, the duration of the pulse potential is between 0.002 second and 0.32 second.

An example of the manufacture of a tooth sample.

Take a cube-shaped enamel (2.2 mm×2.2 mm×2.2 mm); drill a small hole on the bottom surface of the enamel; clean the enamel and then dry the enamel; adhere a copper wire to the hole of enamel; seal parts of the enamel via epoxy resins except the outside surface of the enamel in contact with fluorides.

Simulating Caries Process (pH Cycling)

In vitro caries process (pH cycling) is commonly used in dental caries research, especially for assessing the efficiency of fluorine compounds for preventing teeth from demineralization. This embodiment is designed and developed from a work published in the literature (ten Cate J M, et al., Caries Res 2006; 40:136-41).

From the first day to the third day: immerse the enamel specimen in 4 ml demineralization solution for one hour, wherein the demineralization solution comprises 1.5 mM $CaCl_2$, 0.9 mM $KH_2PO_4$, and 50 mM $CH_3COOH$, with the pH of the demineralization solution fixed between 4.6 and 4.8; use a rinse solution to clean the enamel for five seconds, wherein the rinse solution comprises 1.5 mM $CaCl_2$, 0.9 mM $KH_2PO_4$, and 130 mM KCl; immerse the enamel in 4 ml remineralization solution for eight hours, wherein the remineralization solution comprises 1.5 mM $CaCl_2$, 0.9 mM $KH_2PO_4$, 130 mM KCl, and 20 mM HEPE, with the pH of the remineralization solution fixed at 7; use the rinse solution to clean the enamel for five seconds; and then repeat the above steps for two times.

Import fluorides into the enamel via the electrochemical reaction described below for fluoride iontophoresis as described in electrochemical reaction.

From the fourth day to the sixth day: repeat the steps of demineralization and remineralization described above.

Electrochemical Reaction

Test the conductivity of the enamel specimen using cyclic voltammetry (CV). The test also increases the hydrophilicity of the enamel pores, and then immerses the enamel in NaF solution to import fluorides into the enamel.

Cyclic Voltammetry (CV)

Figure 2:
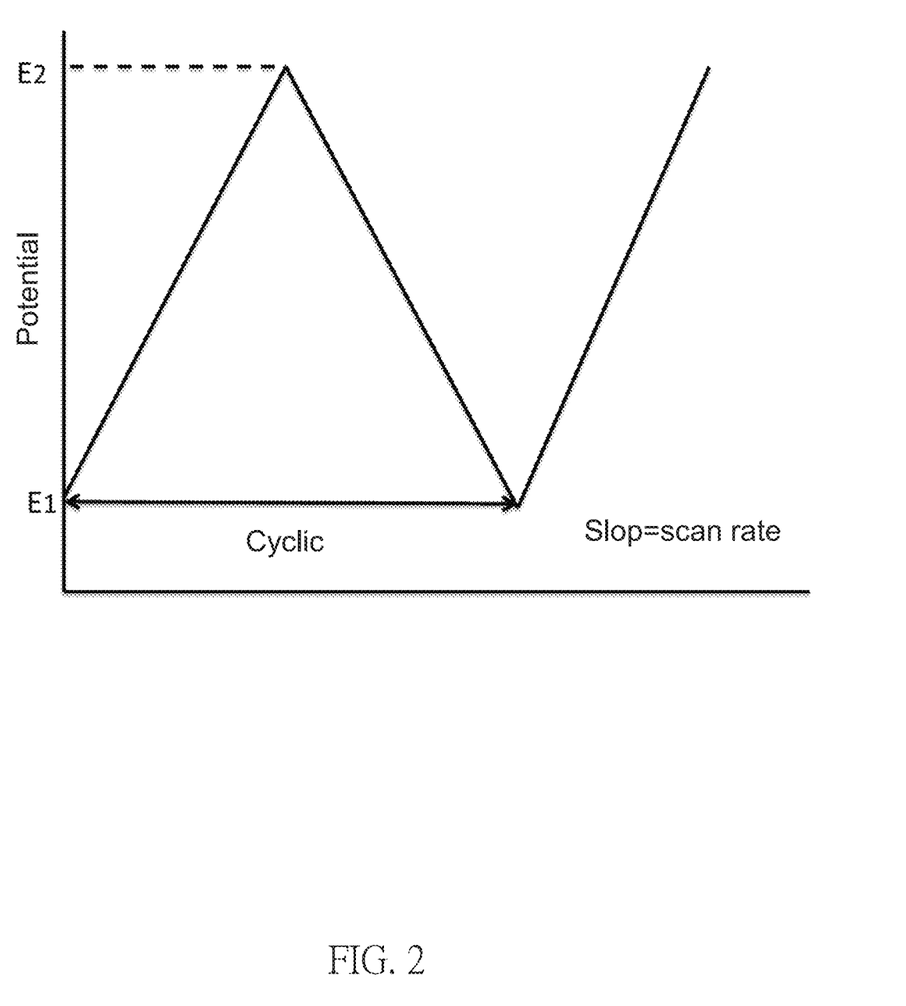
FIG. 2 shows the time function of the potential in cyclic voltammetry (CV)

FIG. 2 shows a time function of potential in cyclic voltammetry (CA).

Figure 4B:
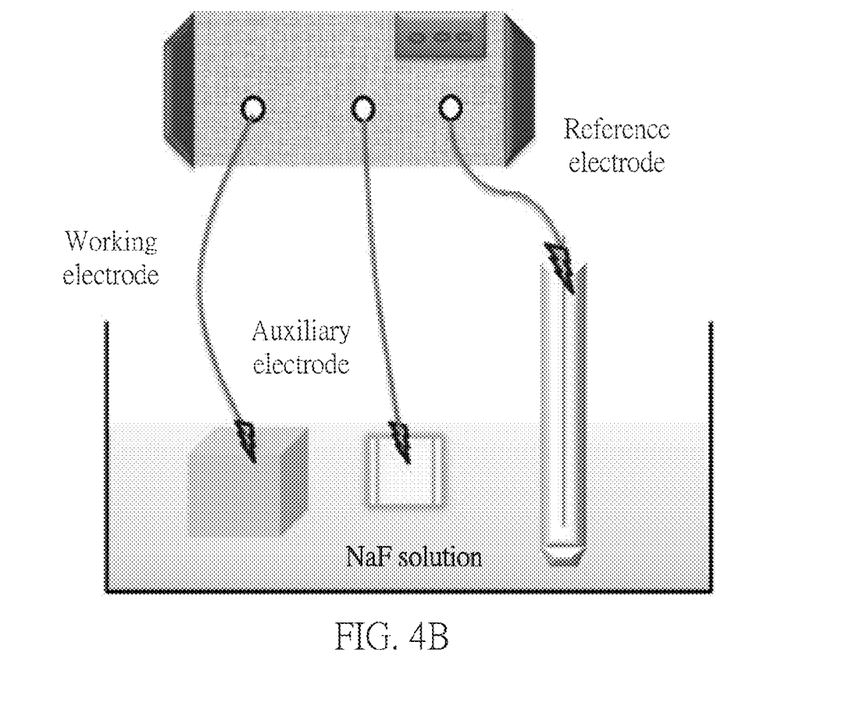

FIG. 4B shows an electrode device (SP150, BioLogic). The reference electrode 13 (Ag/AgCl electrode) is connected to the reference electrode terminal of the power supply, the enamel 15 is connected to the working electrode terminal, and a platinum plate 14 is connected to the auxiliary electrode terminal. The electrolyte solution 17 is NaF solution. The setting of parameters comprising: voltage of −1V~10V and scan rate of 50 my/s.

Pulse Fluoride Iontophoresis Test

Table 1 shows twelve groups of test conditions of the electrochemical approaches.

Pulse amperometry (PA): set different durations for the open-circuit voltage (OCV) and a 10V pulse, and the total reaction time is 100 seconds.

Chronoamperometry (CA): provide 10V continuously without pulse, and the total reaction time is 100 seconds.

TABLE 1

| Group | Duration of OCV (second) | Duration of 10 V pulse (second) | Number of scans | Total reaction time (second) |
| --- | --- | --- | --- | --- |
| OCV-10 V | 0.002 | 0.008 | 10000 | 100 |
| OCV-10 V | 0.005 | 0.005 | 10000 | 100 |
| OCV-10 V | 0.005 | 0.02 | 4000 | 100 |
| OCV-10 V | 0.005 | 0.08 | 1176 | 100 |
| OCV-10 V | 0.005 | 0.32 | 307 | 100 |
| OCV-10 V | 0.008 | 0.002 | 10000 | 100 |
| OCV-10 V | 0.02 | 0.005 | 4000 | 100 |
| OCV-10 V | 0.08 | 0.005 | 1176 | 100 |
| 0 V-10 V | 0.005 | 0.005 | 10000 | 100 |
| 5 V-10 V | 0.005 | 0.005 | 10000 | 100 |
| −5 V-10 V | 0.005 | 0.005 | 10000 | 100 |
| CA | None | 100 | — | 100 |

After simulating the caries process and undergoing the electrochemical approach, the enamel, is analyzed as follows.

Element Analysis

Examine the enamel with X-ray Photoelectron Spectroscopy (XPS). Saw the enamel longitudinally and the test points A, B, C, and D are selected in the longitudinal section of enamel at the respective distances of about 0.1 mm, 0.8 mm, 1.5 mm, and 2.2 mm from the outer surface leave the enamel in a vacuum for three days before performing XPS analysis. The binding energy of XPS is calibrated based on the C1s peak at 284.5 eV as a reference.

Demineralization and Remineralization Tests

Collect the demineralization and remineralization solutions in which the enamel has been immersed, and analyze these solutions with ion chromatography (IC).

Demineralization level=(Initial concentration of the demineralization solution)−(concentration of the demineralization solution after test).

The unit of concentration of the demineralization solution measured by ion chromatography is ppm.

The initial concentration of the demineralization solution is the average of the concentrations of the demineralization solutions obtained between the first day and the third day, and the concentration of the demineralization solution after test is the average of the concentrations of the demineralization solutions obtained at the sixth day.

Remineralization level=(experimented concentration of the remineralization solution after test)−(initial concentration of the remineralization solution).

The unit of concentration of the remineralization solution measured by ion chromatography is ppm.

The initial concentration of the remineralization solution is the average of the concentration of the remineralization solutions obtained between the first day and the third day, and the concentration of the remineralization solution after test is the average of the concentrations of the remineralization solutions obtained at the sixth day.

Calcium net=(Calcium loss)+(Calcium uptake).

Figure 5:
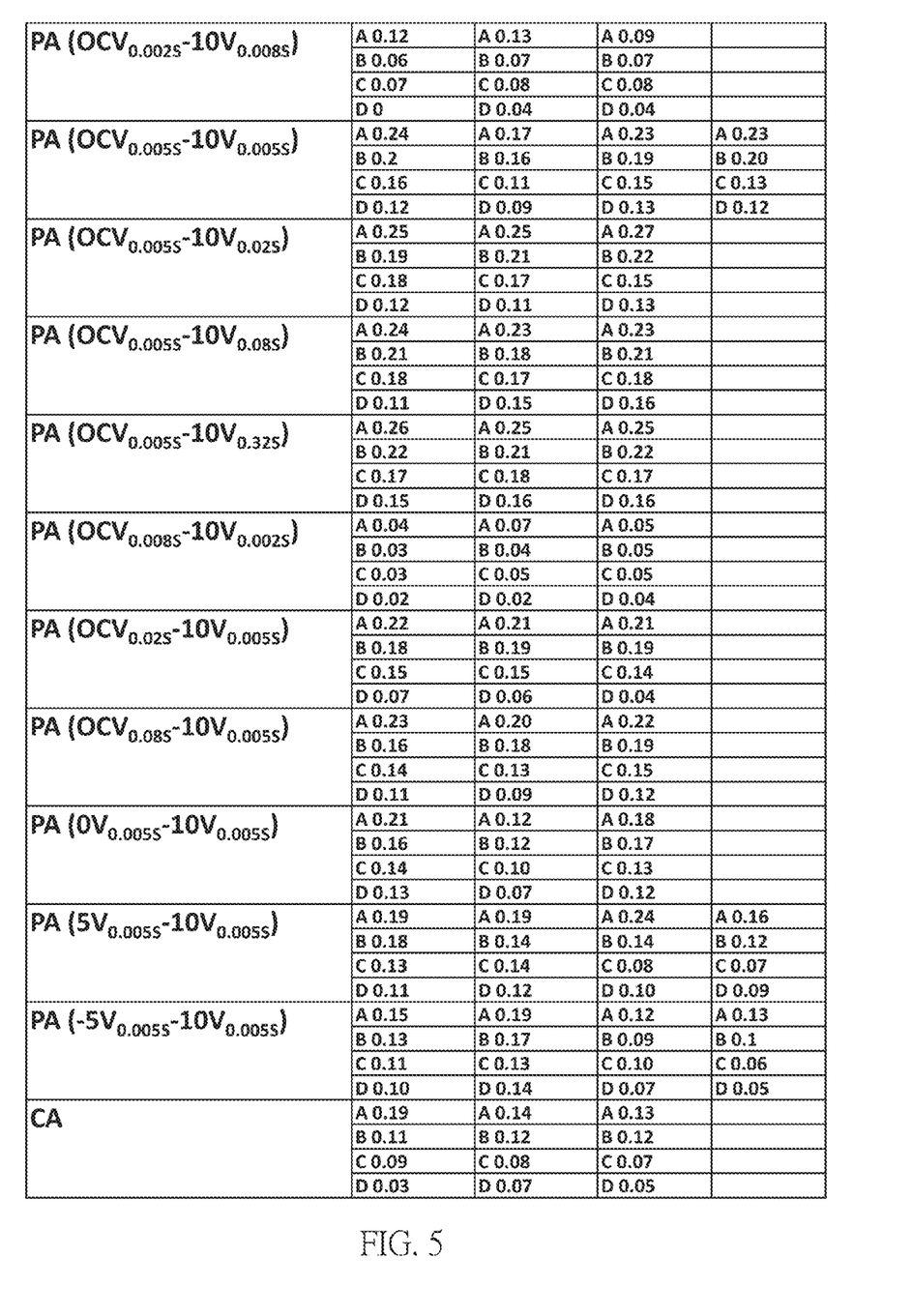
FIG. 5 shows the ratios of F/(Ca+F) obtained in the longitudinal sections of enamel A, B, C, D, which are sampling areas located respectively at the depths 0.1 mm, 0.8 mm, 1.5 mm, and 2.2 mm from outer surfaces, after the enamel specimen undergoing different electrochemical approaches. OCV indicates an open-circuit voltage, PA(xV-yV) indicates the pulse amperometry carried out at xV base potential and yV pulse potential, the suffixes of xV and yV respectively present the durations (in seconds) of xV and yV. The experimental outcomes of different samples are respectively shown in different columns of FIG. 5.

FIG. 5 shows the ratios of F/(Ca+F) of different electrochemical approaches. The ratios are obtained by integrating the peak area of XPS operated, and considering the sensitivity factors of different elements calculated.

As shown in FIG. 5, the F/(Ca+F) ratios obtained from the $PA(OCV_{0.005S}\text{-}10V_{0.005S})$ electrochemical approach are 0.17-0.24, 0.16-0.20, 0.11-0.16, 0.09-0.13 for points A, B, C, D, respectively. These ratios are apparently higher than those of $PA(0V_{0.005S}\text{-}10V_{0.005S})$, $PA(5V_{0.005S}\text{-}10V_{0.005S})$, $PA(-5V_{0.005S}\text{-}10V_{0.005S})$, and CA.

Figure 6A:
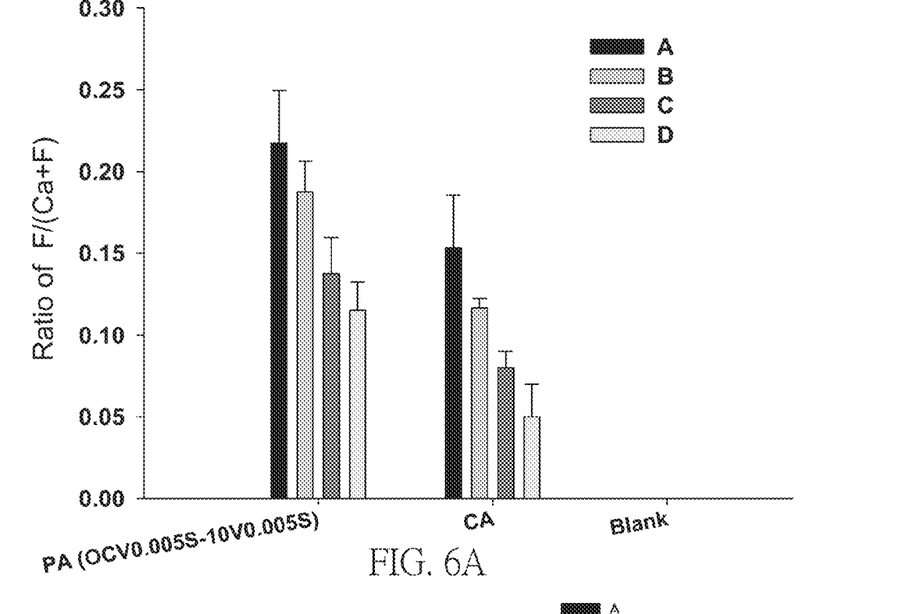
FIG. 6A, FIG. 6B, and FIG. 6C show the ratios of F/(Ca+F) obtained from the specimen undergoing different electrochemical approaches, wherein A, B, C, D are sampling areas located in the longitudinal sections of enamel at the respective depths about 0.1 mm, 0.8 mm, 1.5 mm, and 2.2 mm from the outer surface.
Figure 6B:
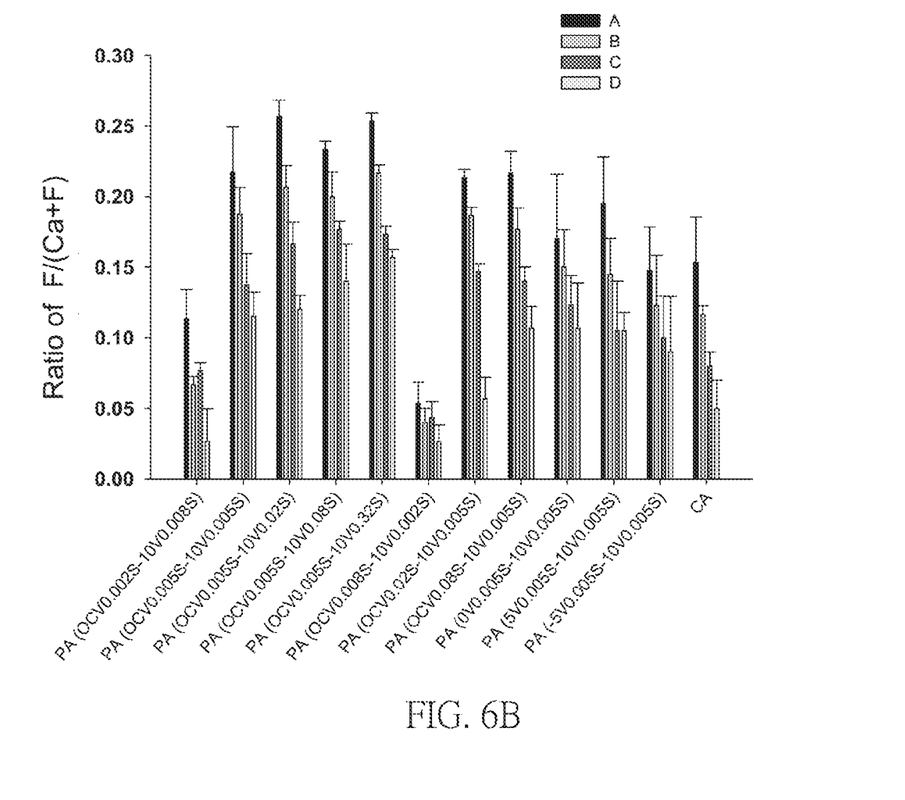
Figure 6C:
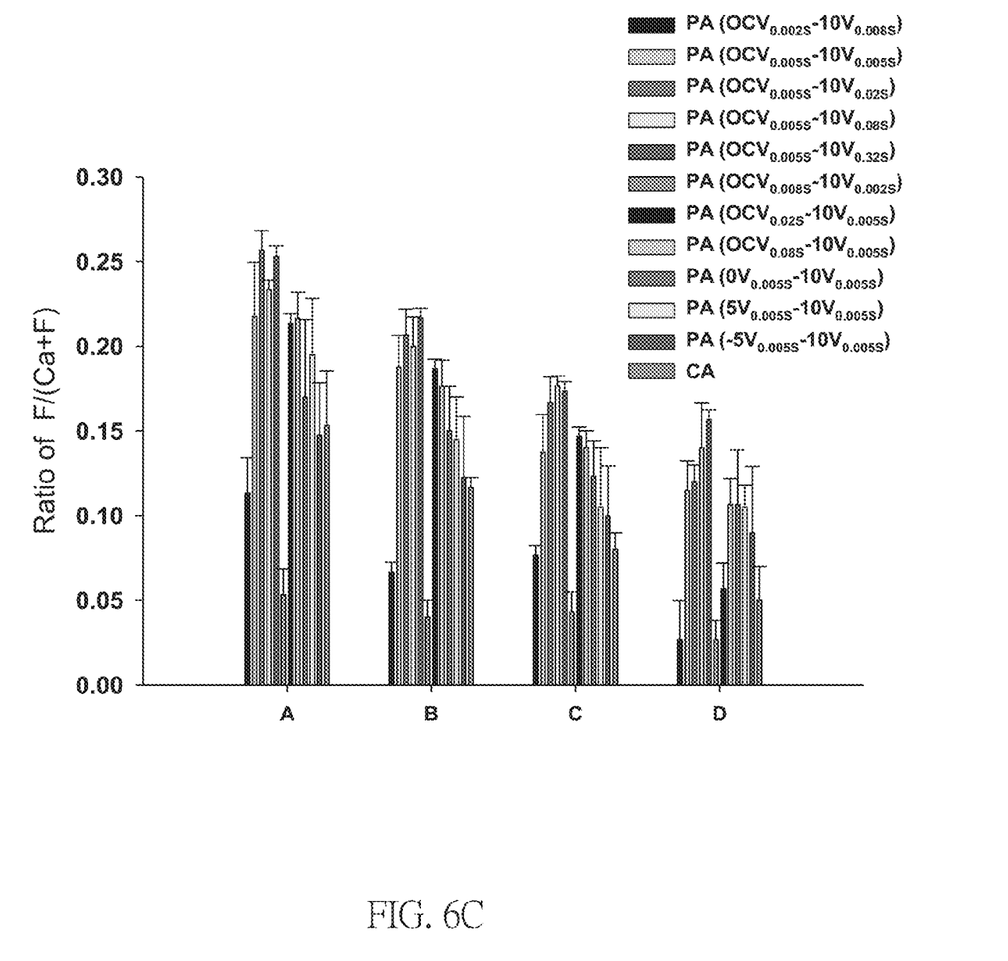

FIG. 6A, FIG. 6B, and FIG. 6C show the F/(Ca+F) ratios obtained after the enamel undergoing different electrochemical approaches. FIG. 6A shows the ratios obtained at points A, B, C, D from each of the electrochemical approaches $PA(OCV_{0.005S}\text{-}10V_{0.005S})$, CA and blank (No fluorides are imported into the enamel). The ratio is zero from the blank approach. When the $PA(OCV_{0.005S}\text{-}10V_{0.005S})$ approach was taken, the ratios at all points are always higher than those at the corresponding points for CA (an electrochemical approach of the current commercial FI device), which confirms that the fluoride iontophoresis with $PA(OCV_{0.005S}\text{-}10V_{0.005S})$ is more effective than that with CA.

FIG. 6B shows the ratios of F/(Ca+F) produced by different electrochemical approaches. As shown in FIG. 6B, the F/(Ca+F) ratios produced at different depths A, B, C, D by $PA(OCV_{0.005S}\text{-}10V_{0.005S})$, $PA(OCV_{0.005S}\text{-}10V_{0.02S})$, $PA(OCV_{0.005S}\text{-}10V_{0.08S})$, and $PA(OCV_{0.005S}\text{-}10V_{0.032S})$ is always higher than those produced at the corresponding depths by $PA(0V_{0.005S}\text{-}10V_{0.005S})$, $PA(5V_{0.005S}\text{-}10V_{0.005S})$, $PA(-5V_{0.005S}\text{-}10V_{0.005S})$, and CA.

FIG. 6C shows that, via ANOVA analysis, there is no statistical difference in the F/(Ca+F) ratios produced at points A, B, C, D by PA(0V-10V), PA(5V-10V), and PA(-5V-10V). However, the ratios produced by $PA(OCV_{0.005S}\text{-}10V_{0.005S})$ and CA are significantly different.

As shown in FIG. 6B, the F/(Ca+F) ratios produced by $PA(OCV_{0.005S}\text{-}10V_{0.02S})$ are higher than those produced by $PA(OCV_{0.005S}\text{-}10V_{0.005S})$ and $PA(OCV_{0.02S}\text{-}10V_{0.005S})$. As shown in FIG. 6C, the F/(Ca+F) ratios produced by $PA(OCV_{0.005S}\text{-}10V_{0.02S})$ are also higher than those produced by $PA(OCV_{0.005S}\text{-}10V_{0.005S})$ and $PA(OCV_{0.02S}\text{-}10V_{0.005S})$.

The analysis of XPS.

FIs

Figure 7A:
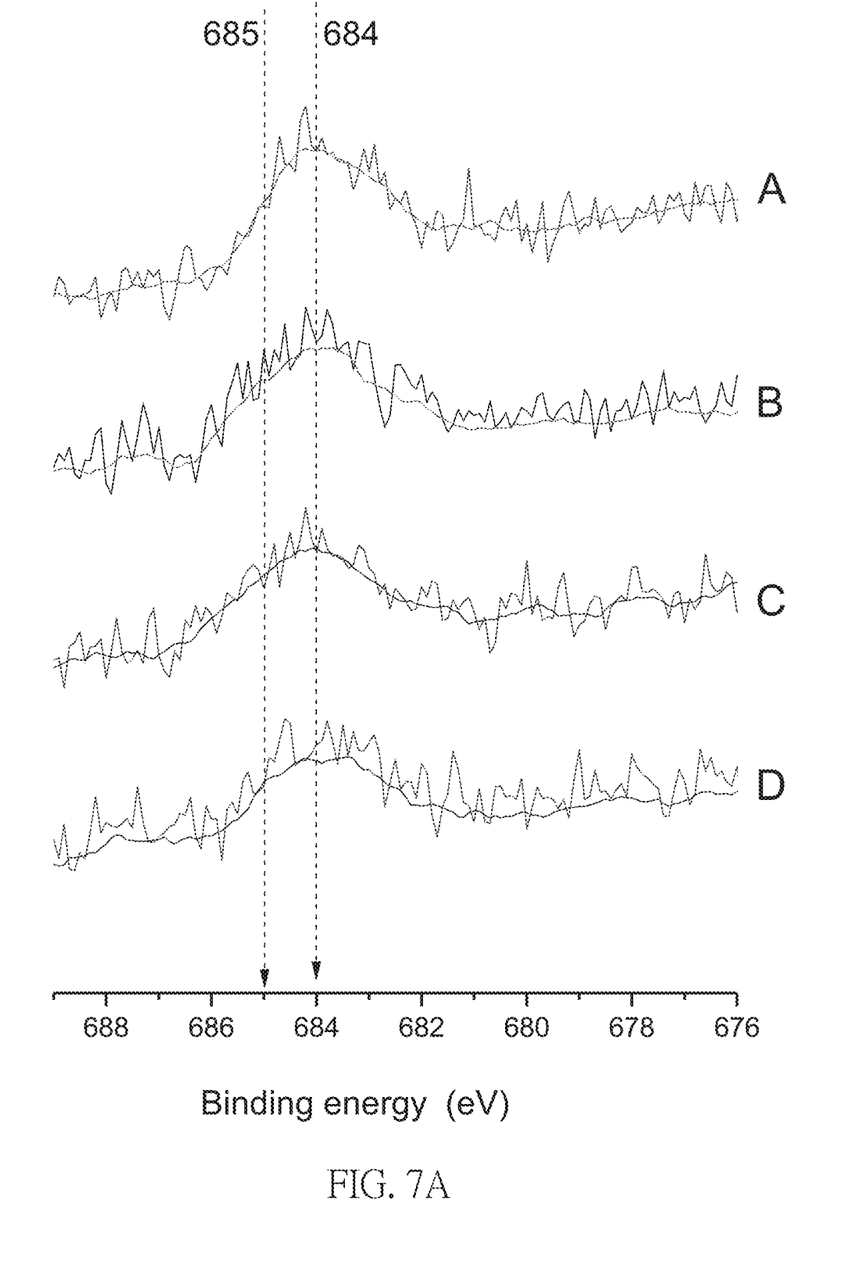
FIG. 7A, FIG. 7B, FIG. 7C, FIG. 7D, FIG. 7E, FIG. 7F, and FIG. 7G respectively show the F is spectra of X-ray photoelectron spectroscopy (XPS) obtained after the specimen undergoing the following respective electrochemical approaches: $PA(0V_{0.005S}-10V_{0.005S})$, $PA(OCV_{0.005S}-10V_{0.005S})$, $PA(OCV_{0.02S}-10V_{0.005S})$, $PA(OCV_{0.005S}-10V_{0.02S})$, $PA(-5V_{0.005S}-10V_{0.005S})$, CA, and blank. A, B, C, D are sampling areas located in the longitudinal sections of enamel at the respective depths of about 0.1 mm, 0.8 mm, 1.5 mm, and 2.2 mm from the outer surface.
Figure 7B:
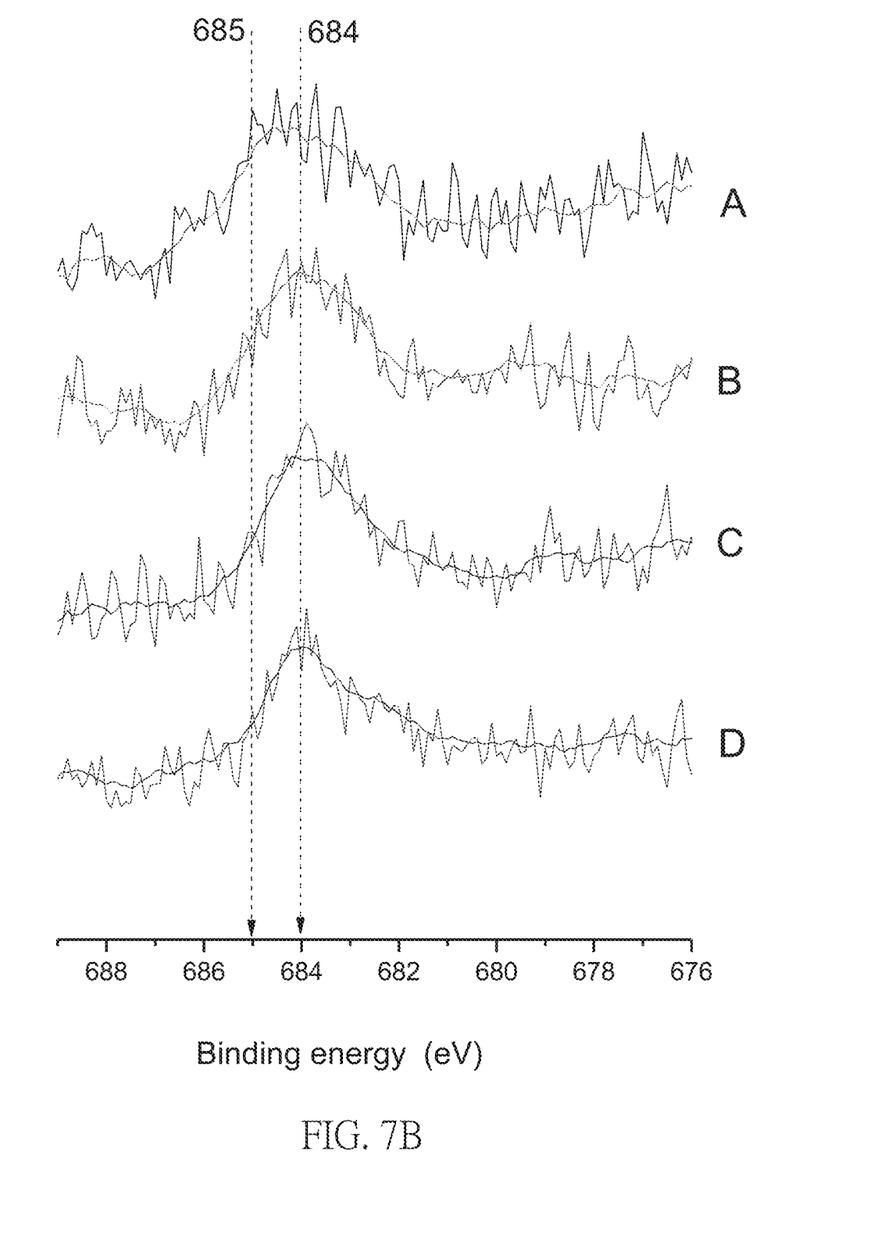
Figure 7C:
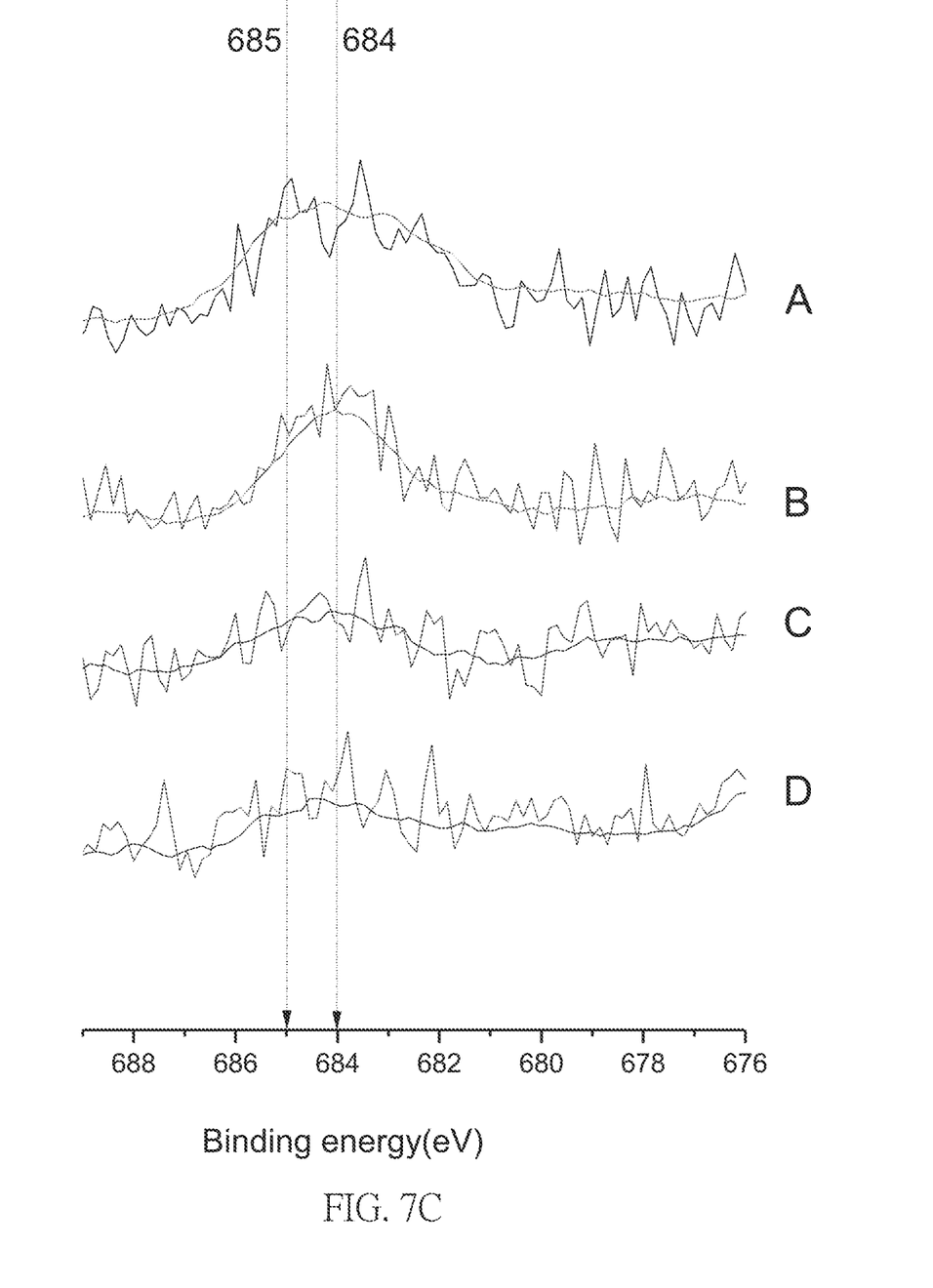
Figure 7D:
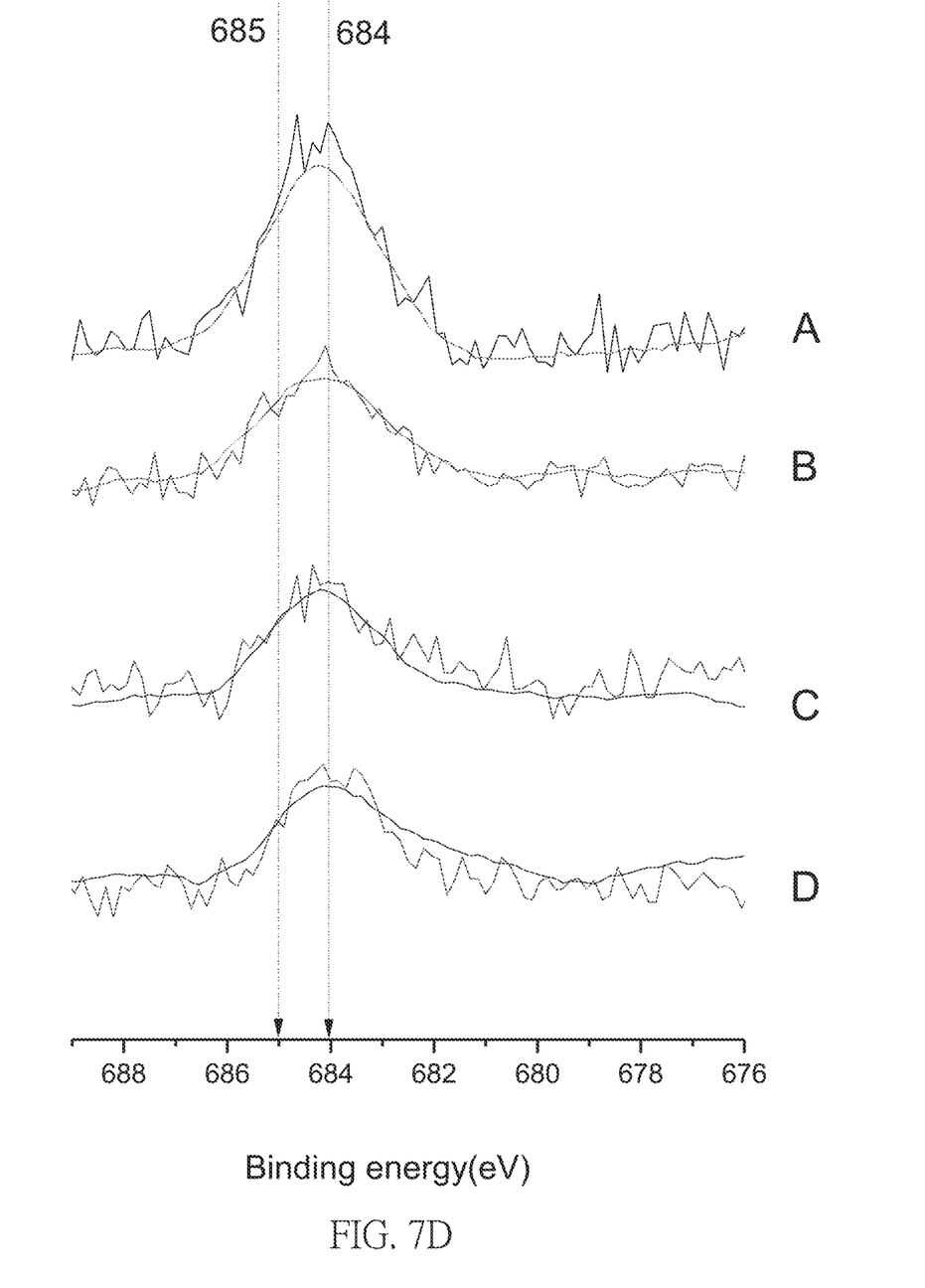
Figure 7E:
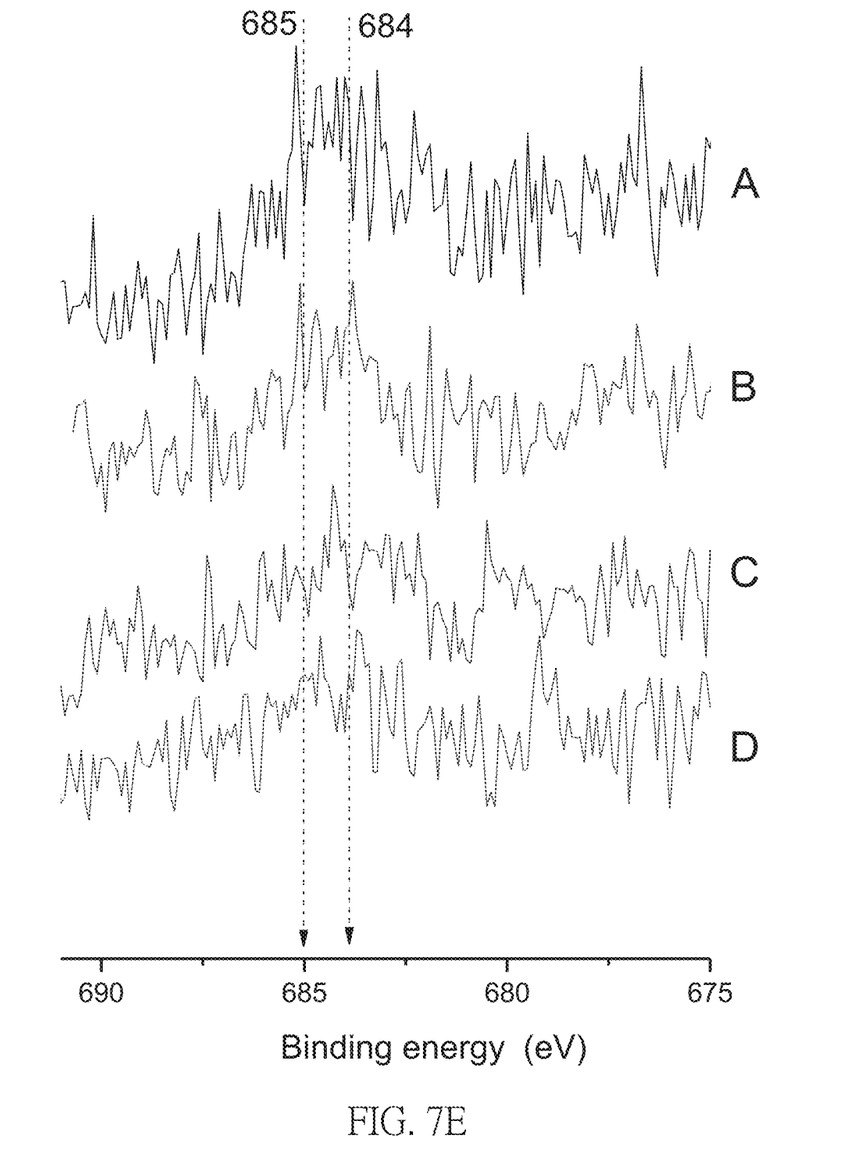
Figure 7F:
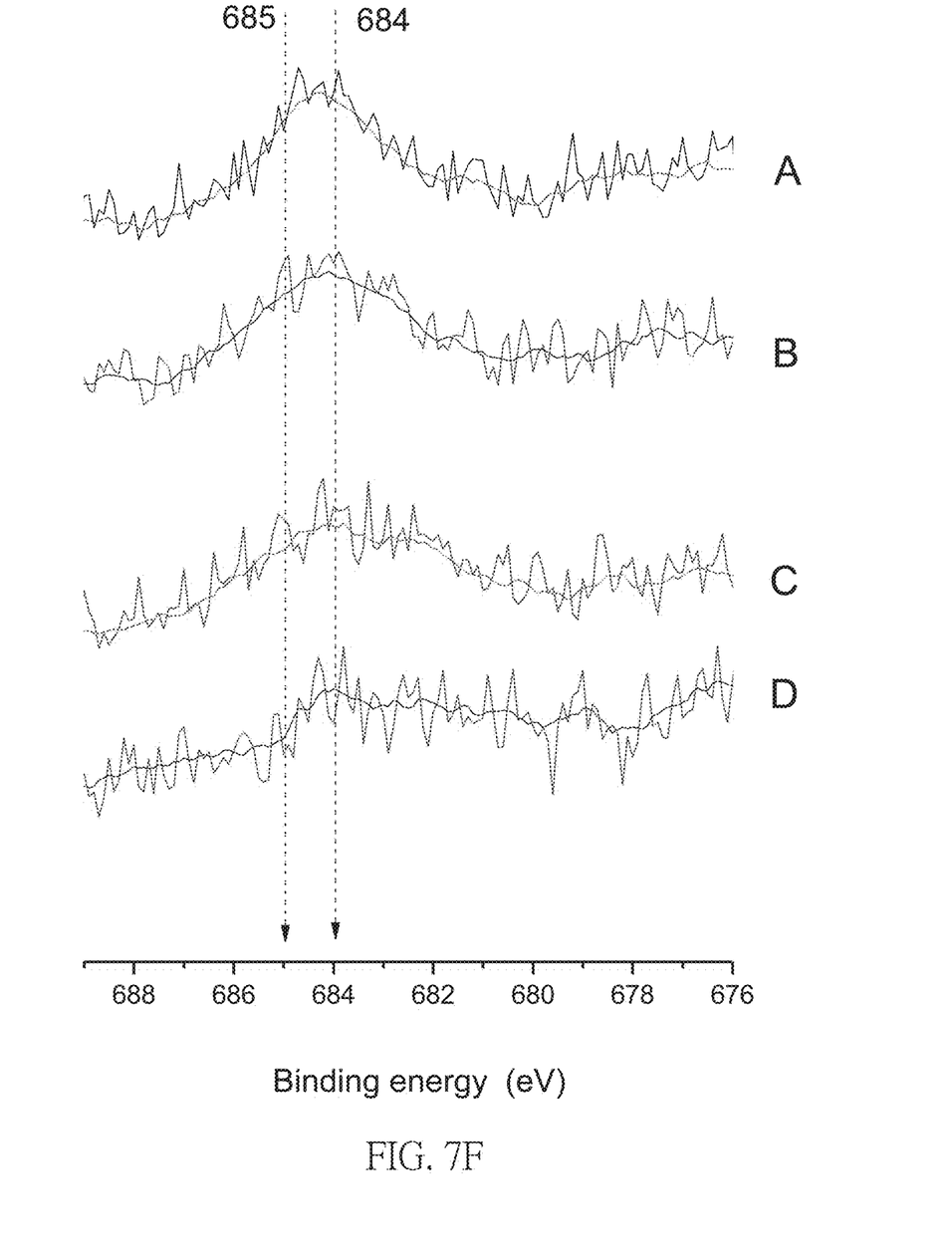
Figure 7G:
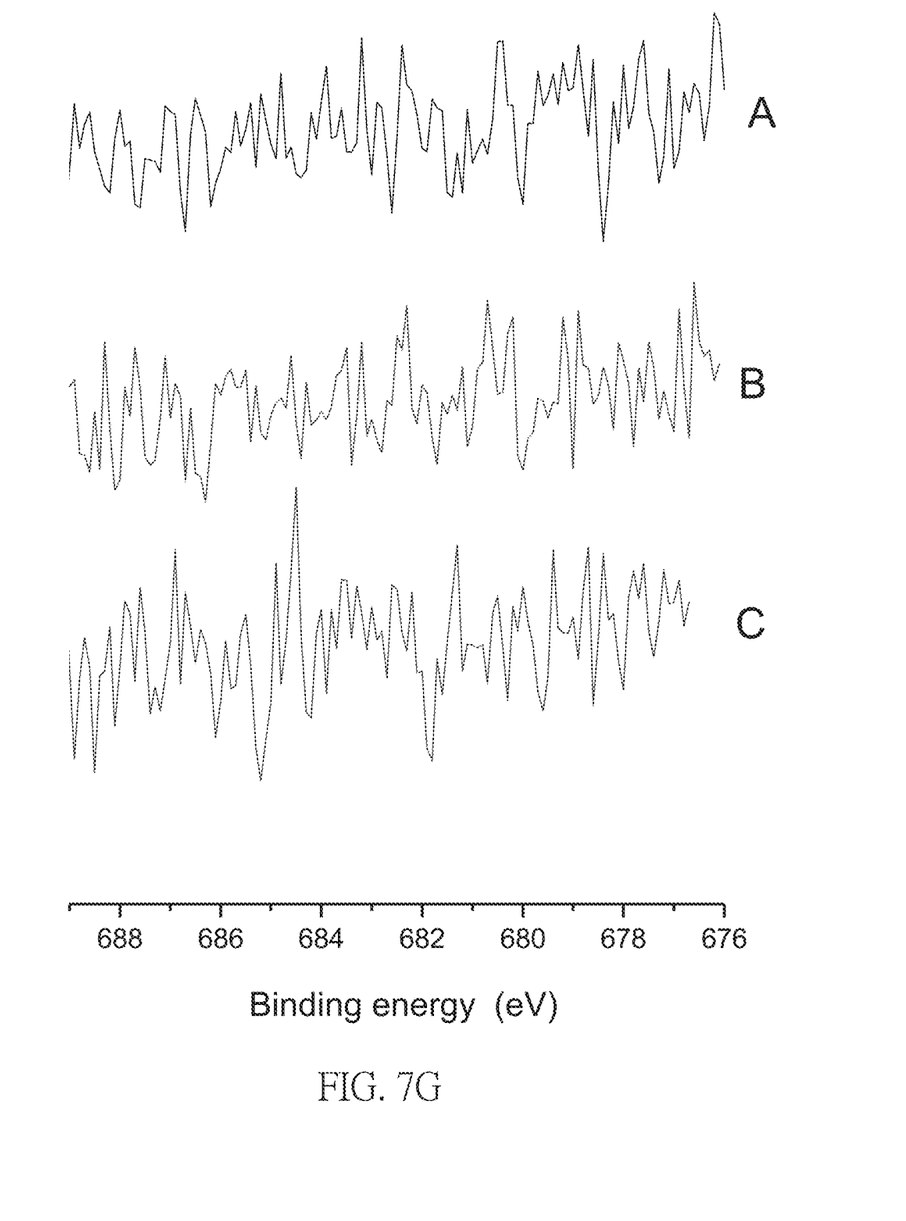

FIG. 7A to FIG. 7G respectively show the binding energies of fluorine analyzed by XPS. FIG. 7A shows the binding energies of fluorine at different depths A, B, C, D in the enamel after it undergoes the $PA(0V_{0.005S}\text{-}10V_{0.005S})$ approach, wherein the binding energies of fluorine is between 684 eV and 685 eV and is closer to 684.1 eV and 684.2 eV. FIGS. 7B, 7C, 7D, 7E, and 7F show the binding energies of fluorine in the enamel after it undergoes, respectively, $PA(OCV_{0.005S}\text{-}10V_{0.005S})$, $PA(OCV_{0.02S}\text{-}10V_{0.005S})$, $PA(OCV_{0.005S}\text{-}10V_{0.02S})$, $PA(-5V_{0.005S}\text{-}10V_{0.005S})$, and CA approaches. From FIG. 7B to FIG. 7F, the binding energies of fluorine is between 684 eV and 685 eV and is also closer to 684.1 eV and 684.2 eV. From FIG. 7A to FIG. 7E, fluorine can be detected from the enamel, wherein the strongest intensity of fluorine is located at point A of the enamel and the intensity of fluorine is decreased with the depth along the longitudinal section. FIG. 7G shows the binding energies of fluorine of the blank. As shown in FIG. 7G, no fluoride is imported into the enamel and no fluorine was found in the enamel.

Ion Chromatography Analysis

Ion chromatography is used to analyze the enamels obtained after it undergoes blank, $PA(OCV_{0.005S}\text{-}10V_{0.005S})$, $PA(-5V_{0.005S}\text{-}10V_{0.005S})$ and CA (provide 10V continuously) approaches, respectively, so as to demonstrate the effect of different electrochemical approaches on enamel for resisting the demineralization and enforcing the remineralization.

Figure 8:
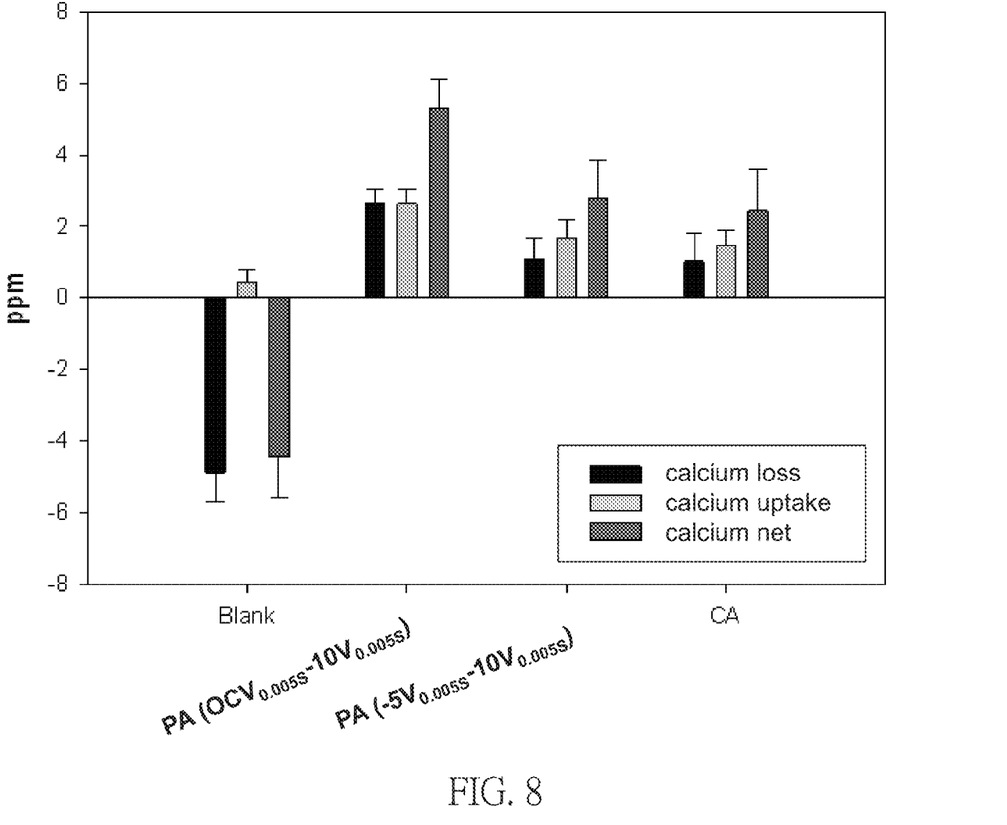
FIG. 8 shows the effect of resisting the demineralization and enforcing the remineralization after enamel specimen undergoing different electrochemical approaches.

As shown in FIG. 8, the effect on enamel for resisting the demineralization and enforcing the remineralization is analyzed by ANOVA.

In the enamel obtained after the blank treatment, the calcium loss is about 5.5 ppm, indicating the negligible effect on enamel from the blank treatment for resisting the demineralization. In the enamel obtained after $PA(OCV_{0.005S}\text{-}10V_{0.005S})$, $PA(-5V_{0.005S}\text{-}10V_{0.005S})$ and CA treatments, the calcium losses were reduced. The $PA(OCV_{0.005S}\text{-}10V_{0.005S})$ treatment, however, give the best effect for the resulting enamel to resist the demineralization. Besides, the effect of remineralization of the enamel can be determined by a calcium uptake of enamel. In the enamel obtained after the blank treatment, the calcium uptake is less than 0.5 ppm. In the enamels obtained after $PA(OCV_{0.005S}\text{-}10V_{0.005S})$, $PA(-5V_{0.005S}\text{-}10V_{0.005S})$ and CA treatments, the calcium uptakes are between 1.5 ppm and 2.5 ppm and are obviously higher than the calcium uptake of the enamel obtained from the blank treatment. The $PA(OCV_{0.005S}\text{-}10V_{0.005S})$ treatment gives the highest calcium uptake, which confirms that pulse fluoride iontophoresis of the present invention can enhance the effect for enforcing the remineralization.

The calcium net (calcium loss+calcium uptake) of the enamel obtained after the blank treatment is a negative value, and the calcium net values of the enamel processed by the pulse iontophoresis of present invention are all positive values, wherein the calcium net of the enamel treated by $PA(OCV_{0.005S}\text{-}10V_{0.005S})$ is 5.3 ppm and is the highest value. It confirms that pulse iontophoresis of the present invention can efficiently prevent the enamel from demineralization and enforce the remineralization of the enamel. It also shows that the PA process is more effective than the CA (an electrochemical approach taken in the current commercial FI device).

The F/(Ca+F) ratio and the effect for resisting the demineralization and enforcing the remineralization are positively correlated. When the F/(Ca+F) ratio is higher, the effect for resisting the demineralization and enforcing the remineralization is more effective. According to the embodiments described above, the ratios of F/(Ca+F) are different for different electrochemical approaches. Overall speaking, the F/(Ca+F) ratios obtained in the enamel undergoing electrochemical approaches of the present invention are better than those obtained from CA (an electrochemical approach taken in the a current commercial FI device). In particular, the F/(Ca+F) ratios obtained from $PA(OCV_{0.005S}\text{-}10V_{0.005S})$, $PA(OCV_{0.005S}\text{-}10V_{0.02S})$, $PA(OCV_{0.005S}\text{-}10V_{0.08S})$, and $PA(OCV_{0.005S}\text{-}10V_{0.32S})$ are significantly higher than the rest.

Besides, the effect for importing fluorides is better than that from the current approach (CA). Fluoride iontophoresis of the present invention can thus be used in clinical applications (prevent teeth from demineralization) more suitably.

The various embodiments in accordance with the disclosed principles have discussed above are for the purpose of describing the present invention. It should be understood that they are presented by way of example only, and are not limiting. Thus, the breadth and scope of the present invention should not be limited by any of the above-described embodiments. Instead, they should be defined in accordance with the claims and their equivalents disclosed in this description. Furthermore, the above advantages and features provided in the described embodiments shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A method for importing fluoride ions into a tooth comprising steps of:
    applying a fluoride iontophoresis device comprising an electrochemical cell device including at least one electrode and a fluoride-containing electrolyte, and a power supply connecting electrically to the electrochemical cell device; wherein at least one electrode contacts with the tooth; and
    providing an electromotive force by the power supply to the electrode to drive the fluoride-containing electrolyte into the tooth; and
    the method is characterized that the power supply provides a periodic pulse voltage to the electrode, wherein the periodic pulse voltage comprises a base potential and a pulse potential, the base potential and the pulse potential being variable over different periods, the base potential being gradually changed to reach the pulse potential with a plurality of steps in each period.

2. The method according to claim 1, wherein the base potential can be elevated to the pulse potential slowly.

3. The method according to claim 1, wherein the ratio of the durations of the base potential and the pulse potential during each of the pulse periods is between 1:64 and 64:1.

4. The method according to claim 1, wherein the duration of the base potential is between 0.001 second and 0.32 second during each of the pulse periods.

5. The method according to claim 1, wherein the duration of the pulse potential is between 0.001 second and 0.32 second during each of the pulse periods.

6. The method according to claim 1, wherein the fluoride-containing electrolyte includes sodium fluoride.

* * * * *